(12) United States Patent
Teich et al.

(10) Patent No.: US 8,697,431 B2
(45) Date of Patent: *Apr. 15, 2014

(54) METHOD AND DEVICE FOR MEASURING MULTIPLE PHYSIOLOGICAL PROPERTIES OF CELLS

(75) Inventors: Jay S. Teich, Berlin, MA (US); Andy C. Neilson, Groton, MA (US); Michael R. Sweeney, Pelham, NH (US); Geoff Uhl, Littleton, CO (US)

(73) Assignee: Seahorse Bioscience, Inc., Billerica, MA (US)

( * ) Notice: Subject to any disclaimer, the term of this patent is extended or adjusted under 35 U.S.C. 154(b) by 156 days.

This patent is subject to a terminal disclaimer.

(21) Appl. No.: 12/782,806

(22) Filed: May 19, 2010

(65) Prior Publication Data

US 2010/0227385 A1 Sep. 9, 2010

Related U.S. Application Data

(60) Continuation of application No. 12/614,773, filed on Nov. 9, 2009, now Pat. No. 7,851,201, which is a division of application No. 11/809,752, filed on Jun. 1, 2007, now Pat. No. 7,638,321, which is a division of application No. 10/688,791, filed on Oct. 17, 2003, now Pat. No. 7,276,351.

(60) Provisional application No. 60/502,417, filed on Sep. 10, 2003.

(51) Int. Cl.
*C12M 1/34* (2006.01)

(52) U.S. Cl.
USPC ..................... 435/287.1; 435/288.4

(58) Field of Classification Search
USPC .......................... 435/287.1, 288.4
See application file for complete search history.

(56) References Cited

U.S. PATENT DOCUMENTS

| | | |
|---|---|---|
| 4,065,357 A | 12/1977 | Groves |
| 4,256,832 A | 3/1981 | Findl et al. |
| 4,461,328 A | 7/1984 | Kenney |
| 4,498,510 A | 2/1985 | Minshew, Jr. et al. |
| 4,599,315 A | 7/1986 | Terasaki et al. |
| 4,711,851 A | 12/1987 | McNamara et al. |
| 4,879,097 A | 11/1989 | Whitehead et al. |
| 5,104,804 A | 4/1992 | Humphries et al. |
| 5,250,419 A | 10/1993 | Bernard et al. |
| 5,278,048 A | 1/1994 | Parce et al. |
| 5,459,300 A | 10/1995 | Kasman |
| 5,468,605 A | 11/1995 | Harris et al. |
| 5,495,850 A | 3/1996 | Zuckerman |
| 5,496,697 A | 3/1996 | Parce et al. |
| 5,536,662 A | 7/1996 | Humphries et al. |
| 5,567,598 A | 10/1996 | Stitt et al. |
| 5,728,541 A | 3/1998 | Kornblith |
| 5,766,875 A | 6/1998 | Hafeman et al. |
| 5,774,214 A | 6/1998 | Prettyjohns |
| 5,792,426 A | 8/1998 | Portmann et al. |
| 5,830,138 A | 11/1998 | Wilson |
| 5,959,297 A | 9/1999 | Weinberg et al. |
| 5,998,517 A | 12/1999 | Gentle, Jr. et al. |
| 6,030,917 A | 2/2000 | Weinberg et al. |
| 6,078,698 A | 6/2000 | Lorton et al. |
| 6,080,574 A | 6/2000 | Berndt |
| 6,083,761 A | 7/2000 | Kedar et al. |
| D438,631 S | 3/2001 | Miller |
| D438,632 S | 3/2001 | Miller |
| D438,633 S | 3/2001 | Miller |
| 6,306,658 B1 | 10/2001 | Turner et al. |
| 6,376,233 B1 | 4/2002 | Wolf et al. |
| 6,380,605 B1 | 4/2002 | Verhaegen |
| 6,395,506 B1 | 5/2002 | Pitner et al. |
| 6,395,555 B1 | 5/2002 | Wilson et al. |
| 6,416,967 B2 | 7/2002 | Kornblith |
| 6,468,736 B2 | 10/2002 | Brooker |
| 6,486,947 B2 | 11/2002 | Modlin et al. |

(Continued)

FOREIGN PATENT DOCUMENTS

| | | |
|---|---|---|
| DE | 4016617 A1 | 11/1991 |
| DE | 4217868 A1 | 12/1993 |

(Continued)

OTHER PUBLICATIONS

Gatti et al. "Oxygen microoptodes: a new tool for oxygen measurements in aquatic animal ecology", Marine Biology, 2002, 140:1075-1085.*

Maharbiz et al. "Silicon microbial bioreactor arrays", Poster 83, 1st Annual International IEEE-EMBS Special Topic Conference on Microtechnologies in Medicine & Biology, Oct. 12-14, 2000, Lyon, France.*

De Beer, "Micro-Electrodes", Immolilized Cells, 2001, Chapter 10, p. 85-100.*

(Continued)

*Primary Examiner* — Bin Shen
(74) *Attorney, Agent, or Firm* — Goodwin Procter LLP

(57) ABSTRACT

A method of analyzing cells disposed in media within a vessel includes the steps of providing a vessel having an original volume of media about the cells, reducing the original volume of media about at least a portion of the cells to define a reduced volume of media, and analyzing a constituent related to the cells within the reduced volume of media. An apparatus for analyzing cells includes a stage adapted to receive a vessel holding cells and a volume of media, a plunger adapted to receive a barrier to create a reduced volume of media within the vessel including at least a portion of the cells, the barrier adapted for insertion into the vessel by relative movement of the stage and the plunger, and a sensor in sensing communication with the reduced volume of media, wherein the sensor is configured to analyze a constituent disposed within the reduced volume.

8 Claims, 8 Drawing Sheets

(56) References Cited

U.S. PATENT DOCUMENTS

| | | |
|---|---|---|
| 6,627,158 B1 | 9/2003 | Peltier |
| 6,653,124 B1 | 11/2003 | Freeman |
| 6,673,532 B2 | 1/2004 | Rao |
| 6,766,817 B2 | 7/2004 | da Silva |
| 6,821,787 B2 | 11/2004 | Neilson et al. |
| 6,835,574 B2 | 12/2004 | Neilson et al. |
| 6,880,158 B1 | 4/2005 | Basso et al. |
| 6,881,584 B1 | 4/2005 | Lenhard et al. |
| 6,887,680 B2 | 5/2005 | Kornblith |
| 6,900,027 B1 | 5/2005 | Kornblith |
| 6,918,404 B2 | 7/2005 | Dias da Silva |
| 6,933,129 B1 | 8/2005 | Kornblith |
| 7,066,586 B2 | 6/2006 | da Silva |
| 7,638,321 B2 | 12/2009 | Teich et al. |
| 7,795,012 B2 | 9/2010 | Lehmann et al. |
| 7,851,201 B2 * | 12/2010 | Teich et al. ............... 435/287.1 |
| 2001/0051353 A1 | 12/2001 | Kornblith |
| 2002/0098592 A1 | 7/2002 | Neilson et al. |
| 2002/0098593 A1 | 7/2002 | Nelson et al. |
| 2002/0132360 A1 | 9/2002 | Neilson et al. |
| 2002/0146345 A1 | 10/2002 | Neilson et al. |
| 2002/0146836 A1 | 10/2002 | Neilson et al. |
| 2002/0168679 A1 | 11/2002 | Naus et al. |
| 2002/0192638 A1 | 12/2002 | Kornblith |
| 2003/0059807 A1 | 3/2003 | Roach et al. |
| 2003/0162285 A1 | 8/2003 | Tajima |
| 2004/0023375 A1 | 2/2004 | Kornblith et al. |
| 2004/0072722 A1 | 4/2004 | Kornblith et al. |
| 2004/0077075 A1 | 4/2004 | Jensen et al. |
| 2004/0086888 A1 | 5/2004 | Kornblith et al. |
| 2004/0107986 A1 | 6/2004 | Neilson et al. |
| 2004/0110301 A1 | 6/2004 | Neilson et al. |
| 2004/0121454 A1 | 6/2004 | Jury et al. |
| 2004/0197905 A1 | 10/2004 | Hafeman |
| 2005/0054028 A1 | 3/2005 | Teich et al. |
| 2007/0037285 A1 | 2/2007 | Ehret et al. |
| 2008/0014571 A1 | 1/2008 | Teich et al. |

FOREIGN PATENT DOCUMENTS

| | | |
|---|---|---|
| DE | 4405375 A1 | 8/1995 |
| DE | 10136005 C1 | 11/2002 |
| DE | 10329983 A1 | 3/2005 |
| EP | 0363262 A1 | 4/1990 |
| EP | 0722136 A2 | 7/1996 |
| EP | 1416041 A4 | 8/2004 |
| FR | 2792333 A1 | 10/2000 |
| WO | WO-94/03583 A1 | 2/1994 |
| WO | WO-9522406 A1 | 8/1995 |
| WO | WO-9815645 A1 | 4/1998 |
| WO | WO-9955827 A1 | 11/1999 |
| WO | WO-9960630 A1 | 11/1999 |
| WO | WO-0032308 A2 | 6/2000 |
| WO | WO-0036410 A1 | 6/2000 |
| WO | WO-00/36410 A9 | 5/2001 |
| WO | WO-0185901 A2 | 11/2001 |
| WO | WO-02/00336 A2 | 1/2002 |
| WO | WO-0202736 A1 | 1/2002 |
| WO | WO-0208385 A1 | 1/2002 |
| WO | WO-0211881 A1 | 2/2002 |
| WO | WO-02061858 A2 | 8/2002 |
| WO | WO-02072423 A1 | 9/2002 |
| WO | WO-02083852 A2 | 10/2002 |
| WO | WO-02099386 A2 | 12/2002 |
| WO | WO-03000557 A2 | 1/2003 |
| WO | WO-03004596 A1 | 1/2003 |
| WO | WO-03059518 A1 | 7/2003 |
| WO | WO-2004065618 A2 | 8/2004 |
| WO | WO-2004094060 A1 | 11/2004 |

OTHER PUBLICATIONS

"The Nature of ATP," *ATP and Biological Energy*, (as printed from Internet on Oct. 4, 2005, http://www.emc.maricopa.edu/faculty/farabee/BIOBK/BioBookATP.html).

Ainscow et al., "Top-down control analysis of ATP turnover, glycolysis and oxidative phosphorylation in rat hepatocytes," Eur. J. Biochem., 263(3):671-85 (Aug. 1999).

Amano et al., "Measuring respiration of cultured cell with oxygen electrode as a metabolic indicator for drug screening," Human Cell 12(1):3-10 (1999).

Andreescu et al., "Autonomous Multielectrode System for Monitoring the Interations of Isoflavonoids with Lung Cancer Cells," 76 Anal. Chem. 8, pp. 2321-2330 (2004).

Andreescu, S. et al., "Advanced electrochemical sensors for cell cancer monitoring," Methods, vol. 37, pp. 84-93 (2005).

B. Cunningham, P. Li, B. Lin, J. Pepper, "Colorimetric resonant reflection as a direct biochemical assay technique," Sensors and Actuators B, vol. 81, p. 316-328, Jan. 5, 2002.

Beebe D.J., Mensing G.A., Walker G.M. (2002) "Physics and applications of microfluidics in biology." Annu. Rev. Biomed. Eng., 4, 261-86.

Beebe D.J., Moore J.S., Bauer J.M., Yu Q., Liu R.H., Devadoss, C., Jo B.H. (2000) Functional hydrogel structures for autonomous flow control inside microfluidic channels. Nature, 404, 588-90.

Bousse, L., Cohen, C., Nikiforov, T., Chow, A., Kopf-Sill, A.R., Dubrow, R. and Parce, J.W. (2000) "Electrokinetically Controlled Microfluidic Analysis Systems." Annu. Rev. Biophys. Biomol. Struct. 29, 155-181.

Brecht & Gauglitz, "Optical probes and transducers," Biosensors and Bioelectronics, 10, p. 923-936, 1995.

Burd et al., "Tumor oxygenation and acidification are increased in melanoma xenografts after exposure to hyperglycemia and meta-iodo-benzylguanidine," Rediation Research 159:328-335 (2003).

Buttgereit et al., "A hierarchy of ATP-consuming processes in mammalian cells," Biochem. J., Nov. 15, 2005;312 (Pt 1):163-7.

Clark, L.C. Jnr. Ann. NY Acad. Sci. 1962; 102:29-45.

Criddle et al. "Simultaneous Measurement of Metabolic Heat Rate, CO2 Production, and O2 Consumption by Microcalorimetry" Analytical Biochem. 1991, 194:413-417.

Deshpande et al., "Microplates with integrated oxygen sensing for medium optimization in animal cell culture," Cytotechnology 46:1-8 (2004).

Ekelund et al., "Microphysiometry: new technology for evaluation of anticancer drug activity in human tumor cells in vitro," Anti-Cancer Drugs 9:531-538 (1998).

Ferguson et al. "Simultaneous monitoring of pH, CO2, and O2 using an optical imaging fiber" Analytica Chemica Acta, 1997, 340: 123-131.

Flora K and J Brennan, "Comparison of Formats for the Development of Fiber-Optic Biosensors Utilizing Sol-Gel Derived Materials Entrapping Fluorescently-Labeled Proteins." Analyst, 1999, 124, 1455-1462.

Ge X, Kostov Y, and G Rao. High Stability non-invasive autoclavable naked optical CO2 sensor. 2003. Biosensor and Bioelectronics 18:pp. 857-865.

Gesinski RM, Morrison JH, Toepfer Jr. "Measurement of oxygen consumption of rat bone marrow cells by a polarographic method." J Appl Physiol. 1968; 24(6):751-754.

Gump et al., "TAT transduction: the molecular mechanism and therapeutic prospects," Trends Mol. Med., 13(10):443-48 (2007).

Guppy, J. Cell Phys. 170:1-7 (1997).

Handbook of Fluorescent Probes and Research Products published by Molecular Probes, Inc., Eugene, Oregon, USA, http://www.probes.com/handbook/ (accessed Mar. 12, 2004), Table of Contents, 2 pages.

Hasselbrink E.F. Jr., Shepodd T.J., Rehm J. (2002) "High-pressure microfluidic control in lab-on-a-chip devices using mobile polymer monoliths." Anal. Chem. 74, 4913-18.

Hua S.Z., Sachs F., Yang D.X., Chopra H.D. (2002) "Microfluidic actuation using electrochemically generated bubbles." Anal. Chem. 74, 6392-96.

Huber et al., "Direct optical immunosensing (sensitivity and selectivity)," Sensors and Actuators B, 6, p. 122-126, 1992.

International Preliminary Report on Patentability for PCT/US2004/029163, Dec. 15, 2005, 15 pages.

International Preliminary Report on Patentability for PCT/US2007/013998, Jan. 22, 2009, 12 pages.

(56) References Cited

OTHER PUBLICATIONS

International Search Report and Written Opinion for PCT/US2004/029163, Mar. 2, 2005, 12 pages.
International Search Report and Written Opinion for PCT/US2007/013998, Apr. 8, 2008, 19 pages.
Invitation to Pay Additional Fees & Partial Internation Search for International Application No. PCT/US2007/013998, mailed Feb. 1, 2008.
Jekabsons et al., "Bioenergetic analysis of cerebellar granule neurons undergoing apoptosis by potassium/serum deprivation," Cell Death Differ. 13(9):1595-610 (Sep. 2006) (Epub Jan. 20, 2006).
Jin et al., "A biosensor concept based on imaging ellipsometry for visualization of biomolecular interactions," Analytical Biochemistry, 232, p. 69-72, 1995.
Jordan & Corn, "Surface Plasmon Resonance Imaging Measurements of Electrostatic Biopolymer Adsorption onto Chemically Modified Gold Surfaces," Anal. Chem., 69:1449-1456 (1997).
Karasinski, J. et al., "Detection and identification of bacteria using antibiotic susceptibility and a multi-array electrochemical sensor with pattern recognition," Biosensors and Bioelectronics, vol. 22, pp. 2643-2649 (2007).
Lehmann, M, Baumann W, Brischwein M, Gahle H-J, Freund I, Ehret R, Dreschler S, Palzer H, Kleintges M, Sieben U and Wolf B. "Simultaneous measurement of cellular respiration and acidification with a single CMOS ISFET. 2001." Biosensors & Bioelectronics. 2001;16:195-203.
Lou et al., "Mitochondrial uncouplers with an extraordinary dynamic range," Biochem J., 407(1):129-40 (Oct. 2007).
Ländesmäki I, Scampavia LD, Beeson C, and Ruzicka J. "Detection of Oxygen Consumption of Cultured Adherent Cells by Bead Injection Spectroscopy." Anal. Chem. 1999; 71: 5248-5252.
McConnell, H.M., Owicki, J.C., Parce, J.W., Miller, D.L., Baxter, G.T., Wada, H.G. and Pitchford, S. (1992) "The Cytosensor Microphysiometer: Biological Applications of Silicon Technology" Science 257: 1906.
Metzger, R., Deglmann, C.J., Hoerrlein, S., Zapf, S. And Hilfrich, J. (2001) Toxicology 166, 97-108.
Morhard et al., "Immobilization of antibodies in micropatterns for cell detection by optical diffraction," Sensors and Actuators B, 70, p. 232-242, 2000.
Motterlini et. al., "Depression of Endothelial and Smooth Muscle Cell Oxygen Consumption by Endotoxin," American Journ. of Physio. vol. 275, No. 168 p. 776-782, Sep. 1998.
O'Riordan TC, Buckley D., Ogurtsov V, O'Connor R., Papkovsky DB "A cell viability assay based on monitoring respiration by optical oxygen sensor." Anal. Biochem. 2000; 278(2):221-227.
Office Action in Chinese Patent Application No. 200480029825, mailed Jul. 18, 2008.
Office Action in Chinese Patent Application No. 200480029825, mailed Nov. 28, 2008 (translation).
Office Action in Indian Patent Application No. 1170/DELNP/2006, mailed Oct. 6, 2008 (translation).
Official Action in European Patent Application No. 04788615.5-1234, dated Mar. 12, 2008, 4 pages.
Owicki, J.C., Bousse, L.J., Hafeman, D.G., Kirk, G.L., Olson, J.D., Wada, H.G. and Parce, J.W. (1994) "The Light-Addressable Potentiometric Sensor: Principles and Biological Applications." Ann. Rev. Biophys. Biomol. Struct. 23: 87-113.
Paitan et al., "Monitoring Aromatics Hydrocarbons by Whole Cell Electrochemical Biosensors," Analytical Biochemistry, 335:175-183 (2004).
Panten U and Klein H. "O2 consumption by isolated pancreatic islets, as measured in a Microincubation system with a Clark-type electrode." Endocrinology 1982; 111:1595-1600.
Parce W, Owicki J, Kercso K, Sigal G, Wada H, Muir V, Bousse L, Ross K, Sikic B, and McConnell H. 1989. "Detection of Cell-Affecting Agents with a Silicon Biosensor." Science. 1989; 246(4927):243-247.
Pattison R, Swamy J, Mendenhall B, Hwang C, and Frohlich B. "Measurement and Control of Dissolved Carbon Dioxide in Mammalian Cell Culture Processes Using an in Situ Fiber Optic Chemical Sensor." 2000. Biotechnology Prog. 16:769-774.
Pouli, A.E., Karagenc, N., Arden, S., Bright, N., Schofield, G.S., Hutton, J.C. & Rutter, G.A. (1998) "A phogrin-aequorin chimaera to image Ca2+ in the vicinity of secretory granules." Biochem. J., 330, 1399-1404.
Prokop et al., "NanoLiterBioReactor: long-term mammalian cell culture at nanofabricated scale," Biomedical Microdevices 6(4):325-339 (2004).
Robiolio et al., "Oxygen diffusion and mitochondrial respiration in neuroblastoma cells," Am. J. Physiol. 256 (6 Pt 1):C1207-1213 (Jun. 1989).
Rumsey et al., "Cellular Energetics and the Oxygen Dependence of Respiration in Cardiac Myocytes Isolated from Adult Rat" Journal of Biological Chemistry. 265(5):15392-15399 (1990).
Scott et al., "Energy transduction in intact synaptosomes. Influence of plasma-membrane depolarization on the respiration and membrane potential of internal mitochondria determined in situ," Biochem. J. 186(1):21-33 (Jan. 1980).
Seaver et al. "Hydrogen Peroxide Fluxes and Compartmentalization inside Growing *Eschericha coli*"J. Bacteriol., 2001, 183: 7182-7189.
Shenoy MA, Biaglow JE, Varnes ME, Hetzel FW. "Inhibition of cultured human tumor cell oxygen utilization by chlorpromazine." Adv Exp Med Biol.1983;159:359-68.
Terada, "Uncouplers of oxidative phosphorylation," Environ. Health Perspect., 87:213-18 (1990).
Thorsen, T., Maerkl, S.J. and Quake, S.R. (2002) Microfluidic Large-Scale Integration Science 298, 580-586.
Tolosa L, Kostov Y, Harms P, Rao G. "Noninvasive measurement of dissolved oxygen in shake flasks." Biotechnol Bioeng Dec. 5, 2002;80(5):594-97.
Unger, M.A., Chou, H-P, Thorsen, T., Scherer, A, and Quake, S.R. (2000) Science 288, 113-116.
Van der Gun et al., "Serum insensitive, intranuclear protein delivery by the multipurpose cationic lipid SAINT-2," J. Control Release, 123:228-238 (2007).
Vanderkooi et. al., "An Optical Method for Measurement of Dioxygen Concentration Based upon Quenching of Phosphorescence, " J. Biol. Chem., 262 (12):5476-5482 (Apr. 1987).
Wada, H.G. Indelicato, S.R., Meyer, L. Kitamura, T., Miyajima, A., Kirk, G., Muir, V.C. and Parce, J.W. (1993) "GM-CSF Triggers a Rapid Glucose Dependent Extracellular Mediated Activation of Acid Production." J. Cell Physiol. 154: 129-138.
Wiley, C and Beeson, C. (2002) "Continuous measurement of glucose utilization in heart myoblasts." Analytical Biochemistry 304, 139-146.
Wilson et al., "The Oxygen Dependence of Mitochondrial Oxidative Phosphorylation Measured by a New Optical Method for Measuring Oxygen Concentration," J. Biol. Chem., 263:2712-2718 (1988).
Wodnicka M, Guarino RD, Hemperly JJ, Timmins MR, Stitt D, Pitner JB. "Novel fluorescent technology platform for high throughput cytotoxicity and proliferation assays." Journal of Biomolecular Screening. 2000; 5:141-152.
Wolfbeis OS, 2002. "Fiber-Optic Chemical Sensors and Biosensors." Annal of Chem. 2002; 74:2663-2678.
"How to Adjust pH Levels," in Office Action mailed Sep. 28, 2010 in U.S. Appl. No. 11/486,440.
Office Action in Chinese Patent Application No. 200780031522.6, dated Jul. 15, 2010 (translation).
Official Action in European Patent Application No. 04788615.5-1234, dated Sep. 8, 2010, 6 pages.
Office Action in Chinese Patent Application No. 200780031522.6, dated Feb. 1, 2011.
Yang et al., "Reversible and repeatable linear local cell force response under large stretches," Experimental Cell Research, Apr. 2005, 305:42-50.
Linder, V., Sia, S., and Whitesides, G. "Reagent-Loaded Cartridges for Valveless and Automated Fluid Delivery in Microfluidic Devices." American Chemical Society 2005; 77(1):6471. (from OA mailed Jun. 21, 2011).

(56) References Cited

OTHER PUBLICATIONS

Office Action in Chinese Patent Application No. 200780031522.6, dated Jul. 29, 2011 (translation).

"Footprint Dimensions", Society for Biomolecular Sciences SBS, ANSI American National Standards Institute, ANSI/SBS 1-2004, Jan. 25, 2006.

"Well Positions", Society for Laboratory Automation and Screening SLAS, ANSI American National Standards Institute, ANSI/SLAS Apr. 2004 (formerly recognized as ANSI/SBS Apr. 2004), Oct. 13, 2011.

Cunningham et al., "Colorimetric resonant reflection as a direct biochemical assay technique," 81 Sensors and Actuators B, pp. 316-328, (Jan. 5, 2002).

Examination Report mailed Aug. 31, 2012 for European Patent Application No. 04788615.5 filed Sep. 8, 2004, 4 pages.

Extended European Search Report mailed Sep. 4, 2012 for European Application Publication No. 2322913A2 published May 18, 2011 7 pages.

International Search Report for International Application No. PCT/US03/38294, Apr. 2004.

* cited by examiner

METHOD AND DEVICE FOR MEASURING MULTIPLE PHYSIOLOGICAL PROPERTIES OF CELLS

RELATED APPLICATIONS

This application is a continuation of U.S. patent application Ser. No. 12/614,773, filed Nov. 9, 2009, which is a divisional application of U.S. patent application Ser. No. 11/809,752, filed Jun. 1, 2007, now U.S. Pat. No. 7,638,321, which is a divisional application of U.S. patent application Ser. No. 10/688,791, filed Oct. 17, 2003, now U.S. Pat. No. 7,276,351, which claims the benefit of U.S. Provisional Application Ser. No. 60/502,417, filed on Sep. 10, 2003; the entire disclosures of all four applications are hereby incorporated by reference.

FIELD OF THE INVENTION

This application relates generally to high throughput screening techniques and, more specifically, to the measurement of the constituents (analytes) of an extracellular medium surrounding living cells. All of the patents, articles, and other references cited herein form a part of this patent application and their respective disclosures are incorporated herein by reference in their entirety.

BACKGROUND

Living cells typically consume nutrients and oxygen from the surrounding medium, and return metabolic byproducts, including ions, carbon dioxide, lactate, and various proteins, to this extracellular environment. The rate of uptake and excretion of these analytes can provide valuable information regarding the metabolic processes underway inside the cells.

Conventional biological assays inherently exhibit significant limitations. An ideal biological assay is homogeneous (i.e., does not require the introduction of a foreign agent such as a dye), non-invasive (i.e., has no deleterious effect on the biological process), and rapid.

Many tools have been developed to probe the mechanistic processes of cells using internalized reporters such as fluorescent dyes. A device that is able to measure extracellular analytes using a non-invasive, homogeneous assay performed within a container that is compatible with existing invasive tools would be particularly useful.

Some previous approaches relate to oxygen flux rate measurements, since respiration can be deemed to be a basic measure of cell viability. Many devices have been developed to monitor respiration in vitro, through determination of the rate of depletion of oxygen in the extracellular medium. The earliest instruments relied on the change in total gas pressure in a sealed vessel, using the assumption that this change was primarily due to oxygen consumption.

In the 1960s, the Clark electrode (Clark, L. C. Jnr. *Ann. NY Acad. Sci.* 1962; 102:29-45), and later the miniaturized Clark electrode, enabled a more specific measure of oxygen partial pressure. The relative complexity of the Clark design, and the fact that the electrode itself consumed oxygen, may have hindered its incorporation in a highly parallel instrument suitable for widespread use. However, these devices were deemed successful enough to measure cell viability (Gesinski R M, Morrison J H, Toepfer J R. "Measurement of oxygen consumption of rat bone marrow cells by a polarographic method." *J Appl Physiol.* 1968; 24(6):751-754), to profile the toxic effects of drugs and chemicals (Shenoy M A, Biaglow J E, Varves M E, Hetzel F W. "Inhibition of cultured human tumor cell oxygen utilization by chlorpromazine." *Adv Exp Med Biol.* 1983; 159:359-68), and to show the effect of agents such as insulin on cellular metabolic processes (Panten U and Klein H. "$O_2$ consumption by isolated pancreatic islets, as measured in a Microincubation system with a Clark-type electrode." *Endocrinology* 1982; 111:1595-1600).

More recently, several oxygen sensors have been developed that can enable the design of a non-invasive, homogeneous readout of cellular respiration. Fluorescent compounds, whose response is diminished by the phenomenon of oxygen-quenching, are now available. These compounds can be embedded in an oxygen permeable membrane and exposed to cell media, and can be read using low cost, fiber coupled, semiconductor light sources and sensors (Wolfbeis O S, 2002. "Fiber-Optic Chemical Sensors and Biosensors." *Annal of Chem.* 2002; 74:2663-2678).

An ion-sensitive field-effect transistor (ISFET), whose gate region can be exposed to a liquid analyte, has been adapted to measure oxygen pressure using enzyme catalyzed conversion of oxygen ($O_2$) to $H^+$ ions that can be detected by this sensor (Lehmann, M, Baumann W, Brischwein M, Gable H-J, Freund I, Ehret R, Dreschler S, Palzer H, Kleintges M, Sieben U and Wolf B. "Simultaneous measurement of cellular respiration and acidification with a single CMOS ISFET. 2001." *Biosensors & Bioelectronics.* 2001; 16:195-203).

Devices have been described and/or demonstrated that incorporate oxygen-quenched fluorophores, ISFETs and other oxygen sensors within sample chambers containing bacteria or mammalian cells for the purpose of measuring respiration rate, viability, or the effect of drugs or toxins. These devices range in size from fluorescent patches attached to the interior wall of large cell culture bottles (Tolosa L, Kostov Y, Harms P, Rao G. "Noninvasive measurement of dissolved oxygen in shake flasks." *Biotechnol Bioeng* 2002 Dec. 5; 80(5):594-7), to fluorescent sensors embedded within microscopic flow cells fabricated using microfluidics technology (Lähdesmäki. I, Scampavia L D, Beeson C, and Ruzicka J. "Detection of Oxygen Consumption of Cultured Adherent Cells by Bead Injection Spectroscopy." *Anal. Chem.* 1999; 71: 5248-5252), to microtitre plates with fluorescent compounds suspended within (O'Riordan T C, Buckley D., Ogurtsov V, O'Connor R., Papkovsky D B "A cell viability assay based on monitoring respiration by optical oxygen sensor." *Anal. Biochem.* 2000; 278(2):221-227) or deposited upon the wells (Woodnicka M, Guarino R D, Hemperly J J, Timmins M R, Stitt D, Pitner J B. "Novel fluorescent technology platform for high throughput cytotoxicity and proliferation assays." *Journal of Biomolecular Screening* 2000; 5:141-152).

Some patents describe a device for monitoring cells using an oxygen-quenched fluorescent compound that is placed in contact with a broth containing bacteria or mammalian cells. A fluorescence measurement of cells treated with a drug or toxin may be compared to a reference, purportedly to determine the effect of the compound on cellular respiration. In an embodiment, cells are contained within a microplate that is exposed to ambient air. Cells are maintained at a low density in order to maintain viability in this configuration, because high cell density would likely result in anoxia, acidification of the media, and contact inhibition. Measurement times may, therefore, typically be tens of hours or days. In addition, the influx of ambient oxygen and lack of control of sample volume may allow only relative measurement to control to be made. In another embodiment, to limit ambient oxygen influx, mineral oil is placed above the cell media. Because cell density is typically quite low, long measurement times are typically required.

A number of patents and publications describe oxygen flux measurement systems incorporating small, closed sample chambers containing high densities of cells. In these devices, an active perfusion system is used to intermittently restore normal levels of dissolved oxygen, pH, and nutrients. None of these systems are designed or configured to enable the user to easily culture cells, maintain their viability, run experiments in parallel with high throughput, or run other types of assays without detaching and moving the cells.

There have also been approaches to measuring cellular acidification rate. Living cells produce protons ($H^+$ ions) as a byproduct of various metabolic processes, including both aerobic and anaerobic respiration. Protons are also produced when ion exchange pumps on the surface of eukaryotic cells are activated as a result of binding of a ligand with a transmembrane receptor or ion channel. In a fixed volume of extracellular media, this proton flux causes a gradual acidification that can be measured using a pH sensor. Thus, an indication of metabolic rate and/or receptor activation can be determined from a precise measurement of extracellular acidification rate.

A number of pH sensors can be applied to the measurement of cell media. In addition to fluorescent and ISFET sensors similar to those described previously, a light addressable potentiometric sensor has been incorporated in an instrument for rapid measurement of proton flux (Parce W, Owicki J, Kercso K, Sigal G, Wada H, Muir V, Bousse L, Ross K, Sikic B, and McConnell H. 1989. "Detection of Cell-Affecting Agents with a Silicon Biosensor." *Science*. 1989; 246(4927): 243-247).

One patent describes a device employing a method for measurement of extracellular acidification (pH) as an indicator of cellular metabolism. In this device, a small sample chamber containing a high density of cells is intermittently perfused with media and closed to allow measurement of the pH change resulting from cellular proton excretion. A series of repetitive stop/flow cycles provides kinetic metabolic rate data. Because the sample chamber, once assembled, is fixed in size and contains a high density of cells, active perfusion is required to prevent cell death from the rapid acidification and depletion of oxygen from the media. The addition of a perfusion system to the device results in the need for relatively complex tubing, pumps, and other features, that create cleaning and sterilization problems for the user. In addition, when cells are to be treated with a drug using this device, the drug may need to be perfused over the cells for a relatively long period of time, thereby consuming large quantities of typically scarce and expensive compounds.

Other extracellular analytes can be measured using non-invasive techniques. Carbon dioxide evolution can be determined from the measurement of carbon dioxide ($CO_2$) partial pressure in the media using various fluorescent sensors (Pattison R, Swamy J, Mendenhall B, Hwang C, and Frohlich B. "Measurement and Control of Dissolved Carbon Dioxide in Mammalian Cell Culture Processes Using an in Situ Fiber Optic Chemical Sensor." 2000. Biotechnology Prog. 16:769-774) (Ge X, Kostov Y, and G Rao. High Stability non-invasive autoclavable naked optical $CO_2$ sensor. 2003. Biosensor and Bioelectronics 18: pp. 857-865).

Other ions and chemical constituents can be measured using non-invasive techniques based on optical or semiconductor sensors. In addition, larger molecules such as proteins can be measured using non-invasive techniques that are sensitive to the binding of these molecules to antibodies that are attached to sensors exposed to the extracellular media (Flora K and J Brennan. Comparison of Formats for the Development of Fiber-Optic Biosensors Utilizing Sol-Gel Derived Materials Entrapping Fluorescently-Labeled Proteins. Analyst, 1999, 124, 1455-146).

Other physical phenomenon that support such sensors are surface plasmon resonance (Jordan & Corn, "Surface Plasmon Resonance Imaging Measurements of Electrostatic Biopolymer Adsorption onto Chemically Modified Gold Surfaces," Anal. Chem., 69:1449-1456 (1997), grating couplers (Morhard et al., "Immobilization of antibodies in micropatterns for cell detection by optical diffraction," Sensors and Actuators B, 70, p. 232-242, 2000), ellipsometry (Jin et al., "A biosensor concept based on imaging ellipsometry for visualization of biomolecular interactions," Analytical Biochemistry, 232, p. 69-72, 1995), evanescent wave devices (Huber et al., "Direct optical immunosensing (sensitivity and selectivity)," Sensors and Actuators B, 6, p. 122-126, 1992), reflectometry (Brecht & Gauglitz, "Optical probes and transducers," Biosensors and Bioelectronics, 10, p. 923-936, 1995) and Wood's anomaly (B. Cunningham, P. Li, B. Lin, J. Pepper, "Colorimetric resonant reflection as a direct biochemical assay technique," Sensors and Actuators B, Volume 81, p. 316-328, Jan. 5, 2002).

In general, the utility of devices incorporating these sensing technologies for the purpose of measuring secretion of proteins by cells is limited by detection sensitivity. Sensitivity can be increased, typically by increasing cell density in the region proximal to the sensor surface. However, cellular health declines rapidly as cell density increases, due to anoxia, acidification of the media, and contact inhibition. It is possible, but generally undesirable, to adhere cells directly to the sensor surface.

A need exists for the provision of a high cell density for measurement of analytes and a low density for maintenance of cell health and growth. While many devices have been developed for the purpose of measuring flux rates of extracellular analytes, there exists a need to meet requirements that may enable widespread use in the fields of biological research, drug discovery and clinical diagnostics. A need exists for devices with high throughput and ease of use. A parallel configuration may be desirable. Preferably, a tradeoff between long assay times and the length of time to prepare the sample would be eliminated. Lack of these attributes may result in low sample throughput and therefore incompatibility with modern drug discovery and diagnostic activities.

In addition, there is a need for an instrument that can be used to measure extracellular flux rates of cells in a non-invasive manner within a vessel that is commonly used for other high throughput assays, thereby allowing the use of the flux rate measurement as a quality control or complementary measurement to existing assays.

In summary, there is a need for a device that can meet the goals of data quality, compatibility with existing experimental practices, and ease-of-use, thereby enabling widespread adoption of a new technology.

SUMMARY

New methods and apparatus have been conceived and developed for providing high cell density for measurement of analytes and low cell densities for maintenance of cell health and growth. The instant invention can determine the flux rates of various extracellular analytes in minutes, can provide quantitative rather than relative readings, can be used without adversely affecting the physiological state of the cells under test, and does not require an active perfusion or agitation system.

One feature of the invention is the temporary creation of a substantially closed sample chamber within a vessel containing a low density mixture of cells and media, and a sensor or plurality of sensors for measurement of analytes. Since a temporary sample chamber is created within a larger vessel, media containing high levels of dissolved oxygen and other analytes, and normal pH, is supplied to the cells prior to, and immediately after a measurement is made. Using this feature, cells can be grown, maintained for extended periods, treated with drug compounds, and assayed using any of a variety of methods, while being periodically assayed for viability and respiration rate, without compromising the cells.

Furthermore, the media containing cells need not be removed from the vessel; it is only displaced temporarily. Therefore, a minimal quantity of drug compound is required.

In addition, by precisely controlling the dimensions of the temporary sample chamber, a quantitative flux rate for extracellular analytes can be determined easily. Therefore, an external reference is not required; a change in the flux rates of cells in a vessel can be determined from multiple readings of this one vessel.

Elements of one embodiment of the invention include:
1. Temporary formation of a small, relatively impermeable sample chamber (containing one or more cells, one or more sensors, and a small amount of cell media) within a larger media-filled vessel.
   This configuration assists with:
   increasing the rate of change of analytes in the media so that a sensitive measurement can be made in a reasonably short time, i.e., minutes vs. hours for some of the prior art methods;
   eliminating the need for a reference, by overcoming the following limitations of the prior art:
     a. Low sensitivity (low cell density in the measurement broth and therefore a small signal that may need to be measured);
     b. Unknown sample volume (user variability in fill level of each well and evaporation); and
     c. $O_2$ influx from the surrounding environment (unless the entire well is sealed with, e.g., a mineral oil coating as suggested by the prior art, which results in a terminal experiment);
   eliminating the need for complex fluidic systems to provide intermittent perfusion to a flow cell, since a high ratio of cells/media is only created temporarily in accordance with the invention; and
   development of a high sensitivity cell-based assay system for other types of sensors, including SPR, SRU, etc., where the analyte affected by the cells is affected at a low rate that is difficult to measure;
2. The specific design of a device to accomplish the above, including a stepped well and inverted, mushroom-shaped probe with optical sensors on the bottom surface; and
3. Temporary insertion of the sensor described above into a variety of vessels (including clear-bottom microplates) containing cells.
   This enables the use of substantially all conventional assays, without the need to move cells or disturb their adhesion to the vessel surface; and
   Sensors can be cleaned and reused in minutes.

It is one object of this invention to provide a rapid, non-invasive, and easy-to-use method for determining various physiological properties of living cells. In particular, a device and method are described that can measure overall cellular metabolic and respirative rates, the relative proportion of aerobic to anaerobic respiration, the relative rates of consumption of various metabolic substrates, the effect of stimulation of certain transmembrane and other cellular receptors, the rates of production of various secreted factors, and cell viability.

The device and method can be applied in a variety of fields, including biological research, drug discovery, and clinical diagnostics. The device can be used as a stand-alone instrument or in conjunction with existing assay methods. For example, as a drug discovery tool, the device can be used to screen various compounds for an effect on cellular metabolism, protein secretion, or intra/extra cellular ion exchange. In addition, the device can be used to replace more complex, invasive, and time consuming methods for determining the toxic effects of compounds on cells or tissue samples. For this purpose, the device eliminates the need for the addition of dyes and incubation of cells. The device can also be used to determine the health of cells or tissue both before and after a conventional assay is performed, thereby improving the performance of such an assay.

In one aspect, the invention includes a method of analyzing cells disposed in media within a vessel. The method includes providing an original volume of media about the cells, reducing the original volume of media about at least a portion of the cells to define a reduced volume of media, and analyzing a constituent related to the cells within the reduced volume of media.

One or more of the following features may be included. The reduced volume of media about the cells may be increased to substantially the original volume. A first concentration of the constituent may be determined, and a second concentration of the constituent may be determined at a predetermined time interval from the determination of the first concentration. A flux rate of the constituent may be calculated based on the first concentration and the second concentration.

The reduced volume may include, for example about 5-50% of the original volume, preferably about 5-20% of the original volume. In some embodiments, the reduced volume may be less than about 5% of the original volume.

The cells may include bacteria, fungus, yeast, a prokaryotic cell, a eukaryotic cell, an animal cell, a human cell, and/or an immortal cell. At least a portion of the cells may be attached to a surface of the vessel. At least a portion of the cells may be suspended in the media. At least a portion of the cells may include living tissue.

The constituent being analyzed may include a dissolved gas (e.g., $O_2$, $CO_2$, $NH_3$), an ion (e.g., $H^+$, $Na^+$, $K^+$, $Ca^{++}$), a protein (e.g., cytokines, insulin, chemokines, hormones, antibodies), a substrate (e.g., glucose, a fatty acid, an amino acid, glutamine, glycogen, pyruvate), a salt, and/or a mineral. The constituent may be extracted from the media by at least a portion of the cells. The constituent may be secreted into the media by at least a portion of the cells.

Analyzing the constituent may include sensing the presence and/or the concentration of the constituent. Analyzing the constituent may include by sensing a first concentration of a first constituent, sensing a second concentration of a second constituent, and determining a relationship between the first concentration and the second concentration. Analyzing the constituent may include sensing a rate of change of a concentration of the constituent.

A sensor in contact with the media within the reduced volume may be used. The sensor may be a fluorescent sensor, a luminescent sensor, an ISFET sensor, a surface plasmon resonance sensor, a sensor based on an optical diffraction principle, a sensor based on a principle of Wood's anomaly, an acoustic sensor, or a microwave sensor.

Analyzing the constituent may include determining a parameter such as cell viability, cell number, cell growth rate, response to at least one of a drug, a toxin or a chemical, detection of an entity, and internalization.

The method may include perfusing additional media through the vessel and/or replenishing the media in the vessel.

Reducing the volume of media may include disposing a barrier in the vessel, typically not causing displacement of the media out of the vessel. At least a portion of the barrier may include a sensor. Alternatively or additionally, the reduced volume of media may include a sensor, such as a fluorophore. At least a portion of the vessel may include a sensor.

The environment of at least a portion of the cells may be altered prior to reducing the original volume of media. The environment may be altered by, e.g., exposing at least a portion of the cells to at least one of a drug, a chemical, or a toxin.

The environment of at least a portion of the cells may be altered after reducing the original volume of media.

The method may include covering the vessel, sealing the vessel, and/or stirring at least a portion of the original volume of media in the vessel.

In another aspect, the invention features an apparatus for analyzing cells. The apparatus includes a stage adapted to receive a vessel holding cells and a volume of media; a plunger adapted to receive a barrier to create a reduced volume of media within the vessel including at least a portion of the cells, the barrier adapted for insertion into the vessel by relative movement of the stage and the plunger, and a sensor in sensing communication with the reduced volume of media, wherein the sensor is configured to analyze a constituent disposed within the reduced volume.

One or more of the following features may be included. The sensor may be configured to analyze the constituent without disturbing the cells. The vessel may include a well disposed in a microplate. The well may include a step. The barrier may be adapted to stir the media prior to analysis of the constituent.

The sensor may be, for example, a fluorescent sensor, a luminescent sensor, an ISFET sensor, a surface plasmon resonance sensor, a sensor based on an optical diffraction principle, a sensor based on a principle of Wood's anomaly, an acoustic sensor, or a microwave sensor. At least a portion of the vessel may include the sensor, the reduced volume of media may include the sensor, and/or at least a portion of the barrier may include the sensor.

The apparatus may include an automated electro-optical measurement system. The apparatus may also include a computer, with the automated electro-optical measurement system being in electrical communication with the computer.

The barrier may be biased relative to the plunger.

In another aspect, the invention features an apparatus for analyzing cells. The apparatus includes a vessel for holding cells and a volume of cell media; a plunger adapted to receive a barrier to create a reduced volume of media within the vessel including at least a portion of the cells, the bather adapted for insertion into the vessel by relative movement of the stage and the plunger without disturbing the cells, such that the reduced volume is less than about 50% of the volume of media; and a sensor in sensing communication with the reduced volume of media, wherein the sensor is configured to analyze a constituent disposed within the reduced volume.

In another aspect, the invention features a plate including multiple wells for holding media and cells. Each of at least a portion of the wells includes a seating surface for receiving a barrier a reduced volume.

One or more of the following features may be included. A shape of the seating surface may be generally planar, arcuate, contoured, tapered, conical, stepped, or interlocking. The reduced volume within each of the wells may vary by less than about 10% of a mean volume of the wells, preferably by less than about 5% of the mean volume of the wells, more preferably by less than about 1% of the mean volume of the wells. The seating surfaces of the wells may each include a step disposed about an inner periphery of a respective well. The steps may lie in a step plane disposed above a bottom plane defined by bottoms of respective wells. The step plane and the bottom plane may be parallel planes. A height of the step plane may be less than about 1 millimeter (mm) above the bottom plane, preferably less than about 200 µm above the bottom plane, more preferably less than about 50 µm above the bottom plane.

A fluorescent sensor may be disposed within at least one of the wells. At least one of the wells may include a transparent bottom. At least one of the wells may include an opaque wall.

In another aspect, the invention features a barrier for analysis of cells disposed in media in a vessel. The barrier includes a body portion for insertion into the vessel, the body portion having a barrier surface for mating with a first surface of the vessel to create a reduced volume.

One or more of the following features may be included. A shape of the barrier surface may be generally planar, arcuate, contoured, tapered, conical, stepped, or interlocking. The barrier may include a cover for mating with a second surface of the vessel.

A sensor may be disposed on the barrier surface for analyzing a constituent of a media disposed about at least a portion of the cells. The sensor may include an optical sensor. The optical sensor may be adapted to sense a fluorophore.

A conductor may be coupled to the sensor and configured to conduct signals therefrom. The conductor may include an optical fiber and may be disposed at least partially in the body portion. The barrier may include a readout for transmitting a signal from the sensor. The readout may be visual, fiber, electronics on a post, and/or a plate reader from the bottom.

The barrier may include a plurality of barriers arranged to be received within a plurality of wells in a microplate.

DETAILED DESCRIPTION

This invention enables the temporary creation of a highly concentrated volume of cells within a larger volume of cell media, in order to allow sensitive measurements of the change in constituents of the media that result from biological activity of the cells. By temporarily, rather than permanently, reducing the media volume (and therefore concentrating the cell/media mixture), cells are exposed to a non-normal environment for only a brief period of time and are therefore not adversely affected by the measurement process.

In one embodiment of the invention, cells are grown or placed on the bottom of a vessel containing sufficient type and volume of media to support growth for an extended period of time. A sample chamber is formed in the bottom of the vessel, consisting of the bottom of the vessel and vertical walls, such that the enclosed volume is sufficient to contain the cells plus a reduced volume of media.

A barrier, having a diameter slightly less than the inside diameter of the vessel, is located above the sample chamber on a movable actuator. Upon actuation, the barrier may be raised above the level of liquid in the vessel, or lowered into the liquid and on to the vessel walls, forming a sample chamber that is relatively impervious to the diffusion of analytes from the sample chamber to and from the bulk media now above the cover.

Figure 1:
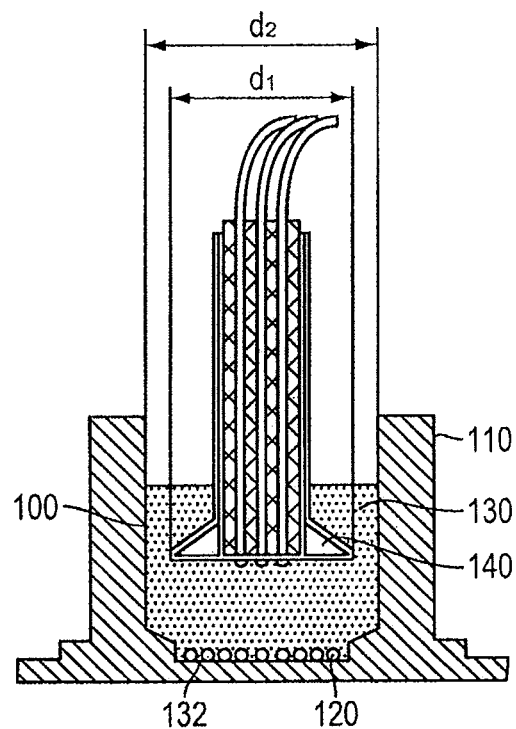
FIG. 1 is a partial cross-sectional view of one embodiment of the present invention, where the vessel is formed by a single well within a multi-well microplate, the cover and sensor assembly being shown in a pre-measurement position.

A cross-sectional view of a representative embodiment is shown in FIG. 1. The drawing details a vessel 100 that is typical of one well 110 within a multi-well microplate. The walls of this single well 110 form the vessel 100 that contains live cells 120 and cell growth media 130. Cells may or may not adhere to a bottom surface 132 of the vessel, and the bottom surface may be treated or coated to encourage adherence. Alternatively, cells may be suspended within the media and may be forced to the bottom of the vessel using gravity or centrifugal force.

Figure 2:
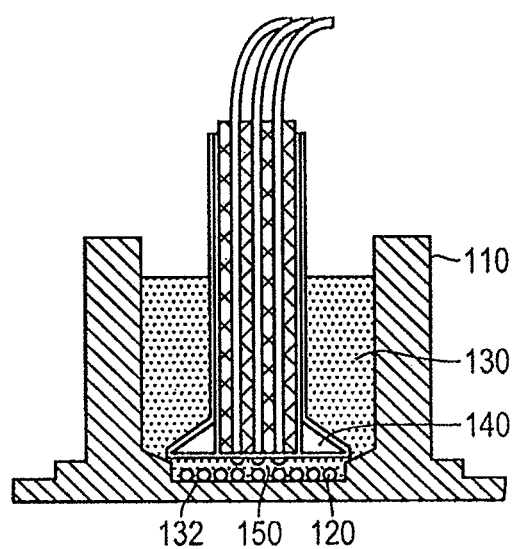
FIG. 2 is a cross-sectional view of the cover and sensor assembly of FIG. 1 in the measurement position.

A barrier 140, having a diameter slightly less than an inside diameter of the vessel 100, is used to form a cover that defines a sample chamber 150 within the vessel. Barrier 140 may have a diameter $d_1$ of, e.g., 6 mm, and vessel 100 may have an inside diameter $d_2$ of, e.g., 7 mm. In FIG. 1, the barrier 140 is shown in a pre-measurement position within the vessel. To effect a measurement, a manual or motorized plunger (actuator) can then be used to reposition the barrier 140 slightly above the bottom surface 132 of the vessel 100 as shown in FIG. 2 by lowering the barrier 140 or raising the well 110. Orienting the barrier to the position shown in FIG. 2 prior to measurement defines the sample chamber 150 having a reduced volume of media, thereby enhancing measurement sensitivity.

A single vessel of nearly any size may be fabricated, or multiple vessels may be fabricated in a one- or two-dimensional arrangement. In one embodiment, a two-dimensional pattern of vessels corresponding to the pattern and dimensions of a microplate, as described by the Society for Biomolecular Screening standards for microplates ("SBS-1 Footprints" and "SBS-4 Well Positions," both full proposed standards updated May 20, 2003), and containing a total of 12, 24, 96, 384, 1536, or any other number of individual wells may be fabricated.

The vessel and sample chamber may typically be formed using plastic material such as, for example, polystyrene or polypropylene, with the bottom clear and the sides colored black to reduce optical cross-talk from one well to another.

A variety of types of barriers may be employed to temporarily reduce the volume of media about the cells without causing displacement of media out of the vessel, such as a simple planar cover lowered vertically, a sliding cover extended horizontally, or a pair of disks with cutouts that can be rotated to act as a valve. It is desirable that the barrier not disturb, i.e., not move, the cells or the media proximal to the cells, in order to reduce the required settling time prior to a measurement.

Figure 3:
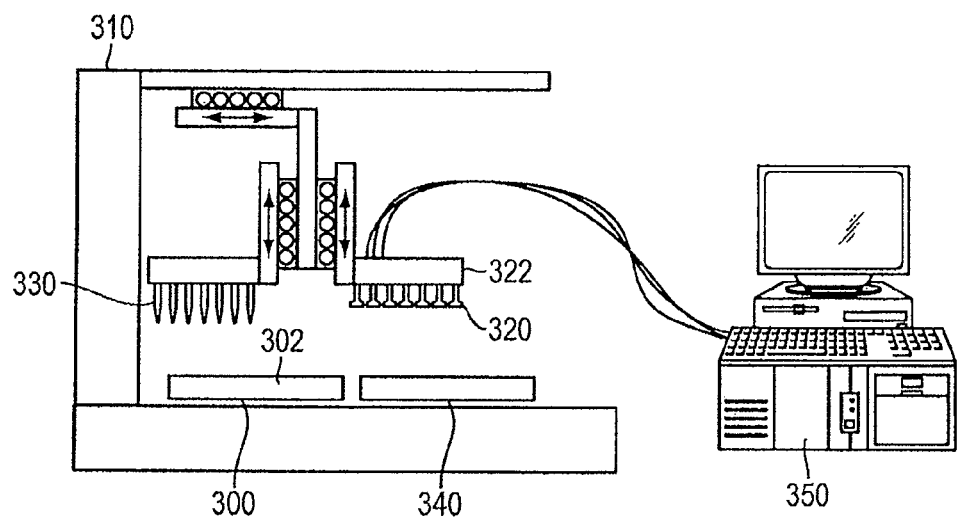
FIG. 3 is a schematic illustration of a complete measurement system, in accordance with one embodiment of the invention.

A complete measurement system can be assembled using the components shown in FIG. 3. A vessel 300, e.g., a plate such as a microplate including a plurality of wells 302, is placed upon a translation stage 310. The microplate is disposed beneath an array of barriers 320 disposed on a plunger 322 adapted to receive the barriers and an array of pipettors 330. Each of at least a portion of the wells includes a seating surface (see, e.g., FIGS. 4a and 4b) adapted to receive one of the barriers. Barriers 320 may include sensors. An original volume of media may be disposed in the wells. Using manual or motorized actuation, the barriers and pipettors may be lowered into the microplate wells to create a reduced volume of media within the wells. The reduced volume may be less than, e.g., 50%, of the original volume of media. The barriers are adapted for insertion into the vessel, i.e., into the wells, by relative movement of the stage 310 and the plunger 322. The barriers and pipettors may also be lowered into one of several fluid reservoirs 340 containing wash buffers and calibrants. When the barriers create the reduced volume of media within the vessels, sensors may be in sensing communication with the reduced volume of media and may be configured to analyze one or more constituents disposed within the reduced volume. The sensors may be interrogated by an optical interface consisting of illumination sources (e.g., light emitting diodes) and light detectors (e.g., photodiodes), with appropriate band-limiting filters interspersed between the optical elements. A computer and software 350 perform actuation, calibration and measurement functions.

A change in the temperature of the media within the sample chamber may result in unwanted measurement errors from at least two sources. First, the capacity of the media to hold dissolved gasses changes with temperature, and therefore a change in temperature may cause an apparent change in dissolved gas concentration as the media seeks equilibrium with the surrounding environment. Second, the measurement properties of many types of sensors changes with temperature.

To ensure accurate and repeatable measurements, the temperature of a reduced volume of media in the vessel may be controlled or a correction factor may be applied to the measurement. Because evaporation induces cooling of the liquid media, control of evaporation may be desired to reduce thermal drift, thermal gradients, and gas exchange.

Providing environmental and temperature control for the sample chamber may reduce unwanted impact on the measurement process. For example, uncontrolled temperature changes of the media surrounding the cells can directly impact the rate of apparent oxygen consumption. Oxygen will naturally off-gas from media as it warms, thus introducing the appearance of a change in cellular respiration when, in fact, the rate change observed is a natural function of dissolved gas seeking equilibrium as the temperature increases. Similarly, any evaporation from the media due to other uncontrolled environmental conditions such as humidity or exposure to air currents can artificially impact the measurements made from various sensors including those of dissolved gases, ions, and temperature.

Using this measurement system, an assay cycle is initiated by mating the sensors/barriers with the vessel walls to form closed sample chambers with reduced volume of media containing the cells. The rate and pattern of actuation of the barriers may be programmed to prevent rapid motion of the media that may disturb the cells, i.e., displace the cells by or cause shear stress on the cells, and may be alternated to provide fluid motion for stirring of the media, as desired.

Additionally, the barriers may be independently biased, for example, by using springs or other force elements, to ensure adequate seating of the covers in all of the wells, simultaneously.

The electro-optical interface and computer are then used to measure the change in response of the sensor or sensors resulting from the change in concentration of extracellular analytes. The rates of consumption or production of analytes may be determined by making multiple readings over a period of minutes and then calculating the slope between selected measurement points. Once the measurement sequence is completed, the sensor/covers are retracted to expose the cells to the full volume of media within each vessel.

The measurement system may include provisions for single or multiple-point calibration of the analyte sensors. For example, two reservoirs containing liquid of known, but different pH, oxygen, $CO_2$, or other analyte levels may be incorporated, and a two-point (gain and offset) calibration may be performed periodically. Alternatively, "factory" pre-calibration of the sensors may be used to eliminate the need for field calibration, or to reduce the calibration to a single point (offset) correction.

Figure 4A:
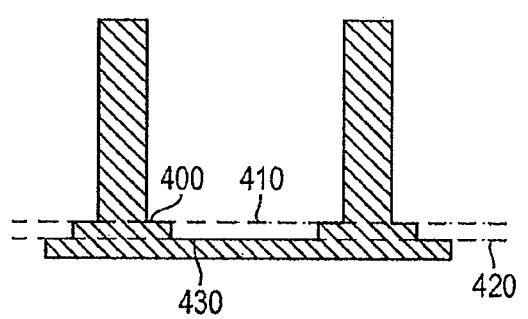
FIGS. 4a and 4b are schematic cross-sectional views of wells with different seating surfaces.

Referring to FIG. 4a, in one embodiment, a microplate is used to provide a plurality of measurement vessels in a standardized pattern. By incorporating a seating surface 400 in each well, a precise reduced volume of media can be maintained about the cells during the measurement period. The reduced volume within each of the wells disposed in a plate may vary by less than about 10% of a mean volume of the wells. In some embodiments, the reduced volume may vary by less than 5% of the mean volume of the wells, and in some embodiments, the reduced volume may vary by less than 1% of the mean volume of the wells. The seating surface 400 or steps may lie in a step plane 410 disposed above a bottom plane 420 defined by bottoms 430 of respective wells, with the step plane 410 and the bottom plane 420 being parallel planes. The height of the step plane is generally less than about 1 mm above the bottom plane and typically less than 50 µm to 200 µm above the bottom plane.

Figure 4B:
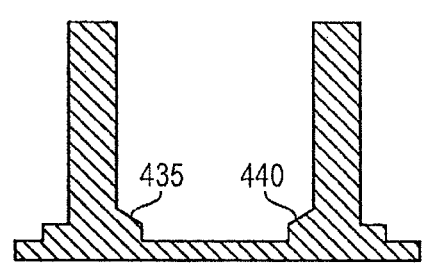

Referring to FIG. 4b, in another embodiment, a sloped surface 435 is incorporated to prevent the adhesion of cells on the seating surface 440. Any of a variety of alternative mating cover and seating surfaces can be employed, in various combinations and permutations, including those that are generally planar, arcuate, contoured, tapered, conical, stepped, interlocking, etc. What is generally desired is that mating features reliably and repeatably isolate the reduced volume from the original volume, such that the reduced volume has a generally predetermined or known capacity. Auxiliary seating components, such as O-rings, or resilient or compliant sealing lips, flaps, or other features may be employed on the covers or in the wells to enhance the seal, as desired.

Figure 5A:
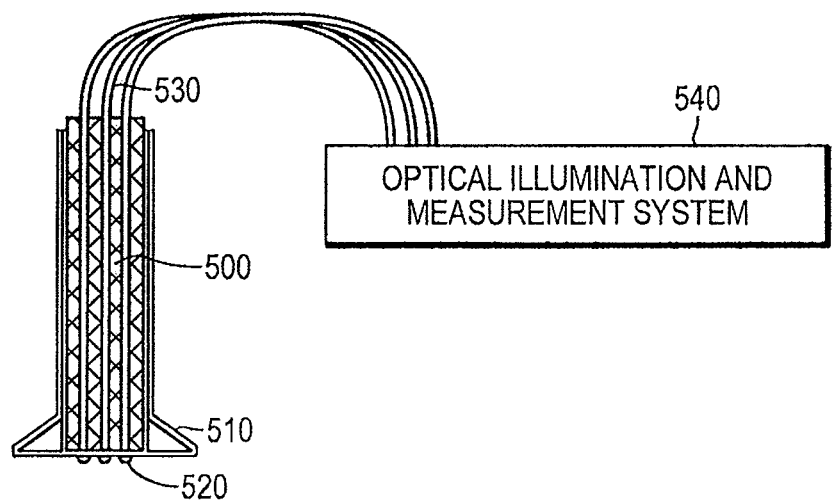
FIGS. 5a-5c are schematic cross-sectional views of barriers that include both a sensor assembly and a readout.

The barrier can be fabricated to include a sensor assembly and a readout for transmitting a signal from the sensor assembly. FIG. 5a shows a cross-sectional view of a barrier formed from the combination of tubular solid support 500 and a removable cover 510 or sheath, having an enlarged distal end that forms a structure upon which one or more optically-coupled sensors 520 are attached. In one embodiment, the sheath may be fabricated from a material that is either disposable or sterilizable in order to prevent contamination of the cell media. A readout 530 may be in the form of optical fibers disposed within the tubular support for communication between the sensors and an electro-optical measurement system 540. The electro-optical measurement system 540 may incorporate a source of illumination, an optical detector, spectral filters, and signal processing components. The electro-optical measurement system 540 may be automated. In some embodiments, the electro-optical measurement system 540 may be in electrical communication with computer 350 (see FIG. 3).

Figure 5B:
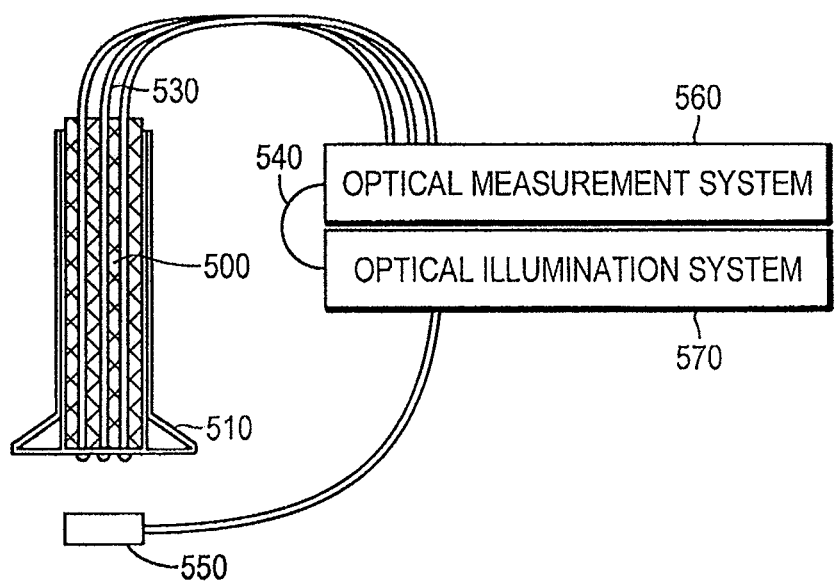
Figure 5C:
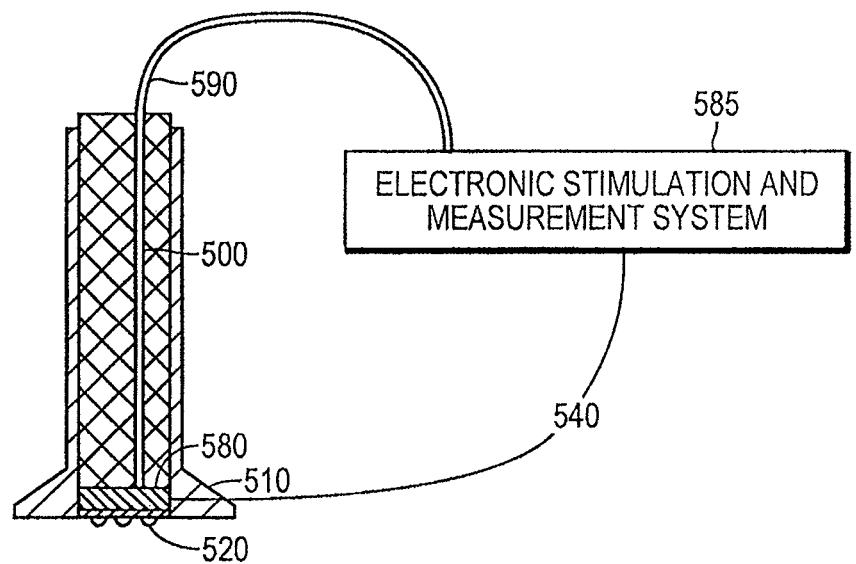

FIG. 5b shows an alternative arrangement in which the sensors are illuminated by an external light source 550. Electro-optical measurement system 540 may include separate components, i.e., an optical measurement system 560 and an illumination system 570. The optical measurement system 560 and illumination system 570 may be automated. In some embodiments, the optical measurement and illumination systems 560, 570 may be in electrical communication with computer 350. Referring to FIG. 5c, in an alternative embodiment, the electro-optical measurement system 540 includes optical and measurement components 580 located within the tubular support 500 and an external electronic measurement system 585. The optical and measurement components may communicate with the external electronic measurement system 585 through a cable 590.

Any form of signal communication can be employed, as desired. Such forms of signal communication might include simple visual interrogation of a signal change such as a change in color; fiber optic signal communication coming from any side of the vessel; a laser or CCD-based plate reader interrogating the signal from the bottom of a transparent vessel.

In practice, many different configurations of vessels, barriers, and sensors may be employed. The total vessel volume may range from many liters to a fraction of a microliter (ml), but is generally less than about 1 ml. The ratio of the reduced volume of media enclosed within the temporary sample chamber to an original volume of media provided in the vessel may range from about 50% to less than about 5% and even as low as less than about 1%, but is typically in the range of 5-20%.

Many different types and numbers of cells can be analyzed, including bacteria, fungus, yeast, prokaryotic and eukaryotic cells, animal or human cells, etc. Cells may adhere to the vessel wall or may be suspended within the media. Immortalized cells, native and primary cells, and homogenized or sliced tissue may be analyzed. A centrifuge may be used to concentrate cells within the sample chamber region of the vessel.

Any number of constituents of the media may be analyzed, including dissolved gasses, ions, proteins, metabolic substrates, salts and minerals. These constituents may be consumed by the cells (such as $O_2$), or may be produced by the cells either as a byproduct (such as $CO_2$ and $NH_3$) or as a secreted factor (such as insulin, cytokines, chemokines, hormones or antibodies). Ions such as $H^+$, $Na^+$, $K^+$, and $Ca^{++}$ secreted or extracted by cells in various cellular metabolism processes may also be analyzed. Substrates either consumed or produced by cells such as glucose, fatty acid, amino acids, glutamine, glycogen and pyruvate may be analyzed. Specialized media may be used to improve the sensitivity of the measurement. For example, the change in pH resulting from extracellular acidification can be increased by using a media with reduced buffer capacity, such as bicarbonate-free media.

The analysis performed using this method may simply detect the presence of a constituent in the media, or may quantitatively analyze the amount and change in concentration, volume, or partial pressure of a constituent. With the incorporation of multiple sensors, one or more ratios of constituents may be analyzed. As an example, the ratio of anaerobic to aerobic respiration utilized by the cell can be determined from a calculation of the ratio of oxygen consumption to extracellular acidification rate that is enabled by a measurement of changes in oxygen partial pressure and pH of the extracellular media. Analysis may include sensing a first concentration of a first constituent, sensing a second concentration of a second constituent, and determining a relationship between the first concentration and the second concentration.

The type of sensors utilized include oxygen sensors, such as oxygen-quenched fluorescent sensors, enzyme-coupled ISFET sensors, miniature Clark electrodes, or other oxygen sensors; pH sensors, including fluorescent sensors, ISFET sensors, pH sensitive dye sensors, LAP sensors, or other pH sensors; $CO_2$ sensors, including bicarbonate buffer coupled and ammonium dye coupled fluorescent sensors as well as other $CO_2$ sensors; various ion and small molecule sensors; large molecule sensors including surface plasmon resonance sensors and sensors exploiting the principle of Wood's anomaly; acoustic sensors; and microwave sensors.

The method may be used to measure any number of attributes of cells and cellular function. For example, cell viability and metabolic rate may be determined from measurements of oxygen consumption rate, extracellular acidification rate, or other metabolic analyte fluxes. By comparison of one or more analyte flux rates to a known rate per cell, cell number may be determined and therefore growth rates can be monitored.

The number of sensors used may range from one to many hundreds. Sensors for dissolved gasses may be placed within the sample chamber, but not in direct contact with the media. Other sensors, however, should be in direct contact with the media and in close proximity to the cells. This may be accomplished by mixing an indicator compound, e.g., a fluorophore, with the cell media, or by embedding the indicator in a compound that is permeable to the analyte to be measured. The embedded indicator may then be attached to any surface of the sample chamber region of the vessel.

In one embodiment, one or more sensors may be attached to the lower surface of the barrier, so as to be exposed to the extracellular media upon lowering of the barrier. One example of a sensor for this purpose is a fluorescent indicator, such as an oxygen-quenched fluorophore, embedded in an oxygen permeable substance, such as silicone rubber.

Sequential measurements of a single group of cells may be made at predetermined time intervals to analyze the effect of changes in the extracellular environment on their function, for example to examine the effect of exposure to a drug, chemical, or toxin. In this method, the volume of media surrounding the cells is first reduced, the constituents of the media are measured, and the volume is restored to its original value, as previously described. The environment surrounding the cells is then altered, such as by adding a chemical that activates a transmembrane receptor, changing the dissolved oxygen level, or adding a nutrient. One or more additional measurement cycles are then performed using the temporarily reduced volume method, to analyze the effect of the altered extracellular environment.

At any time during the sequence of measurements, the cell media may be replenished. In this way, sequential measurements can be made over a period of minutes, hours, or days. Any one of several different approaches may be followed to replenish the media. Media may be replenished by substantially removing part or all of the media within the full volume of the vessel using standard manual or automated pipetting instruments. Alternatively, media may be replenished only within the reduced volume of the vessel when a barrier is lowered into position. In the latter method, media may be replenished by fluidic extraction and delivery from a top side of the vessel through a portal in a plunger mechanism or through a portal built into any one of the sides or bottom of the vessel.

The introduction of an environment altering constituent such as a chemical, dissolved gas or nutrient may also be applied either to the full volume of the vessel as noted above or alternatively to only the reduced volume of the vessel. In the latter embodiment, the volume of media surrounding the cells is first reduced, the constituents of the media are measured, and the volume is restored to its original value, as previously described. The volume is then again reduced and the environment immediately surrounding the cells within only the reduced volume is then altered, by the addition of a constituent through a portal in the plunger or elsewhere in the vessel defining the reduced volume. One or more measurements are made in the presence of the constituent. After this measurement cycle, the media within the reduced volume may be exchanged one or more times to flush out the constituent before exposing the cells once again to the full original volume. This approach may provide a benefit of reducing the volume of compound required. It may also provide the possibility of studying isolated effects without contaminating the entire volume, thereby, in effect, simulating a flow system in wellplate format.

EXAMPLES

The following examples illustrate certain exemplary and preferred embodiments and applications of the instant invention, but are not intended to be illustrative of all embodiments and applications.

Example 1

Repetitive Measurement of the Basal Respiration and Acidification Rates of C2C12 Myoblasts A prototype device was fabricated in order to evaluate various properties and potential applications of the invention.

The device included a cylindrical vessel, fabricated from polycarbonate material, and designed to receive a 12 mm diameter, polycarbonate membrane assembly (Corning Snapwell™ P/N 3802) with a pore size of approximately 3 µm. A cylindrical polycarbonate cover could be temporarily inserted into the vessel to form a smaller sample chamber, approximately 1.5 mm high, with a volume of about 160 microliter (μl). A series of bores around the perimeter of the vessel allowed the insertion of three 500 μm diameter optical fibers. The distal tip of each optical fiber was coated with a fluorescent sensing material to form a biosensor.

The three biosensors were designed to measure the partial pressures of $O_2$ and $CO_2$, and the pH of the media contained within the vessel. One fiber tip was coated with a matrix of Ruthenium dyes, encapsulated in oxygen permeable silicone rubber, to provide a readout of dissolved oxygen concentration. A second fiber tip was coated with a complex of Fluorescence dye encapsulated in silicone rubber, to provide a readout of $H^+$ ion concentration (pH). A third biosensor was fabricated by using a $CO_2$ permeable membrane to create a small reservoir of $NaHCO_3$ surrounding a HydroxyPyrene Trisodium Salt (HPTS) pH sensitive dye. A change in $CO_2$ concentration in the cell media would then cause a change in pH of this encapsulated reagent resulting in a measurable change in the fluorescent properties of the pH sensitive dye, and this change was calibrated to provide quantitative $CO_2$ concentration data.

Light emitting diodes were used to illuminate the three optical sensors at various wavelengths as shown in Table 1, in terms of nanometers (nm). Also shown in Table 1 are the wavelengths used to sense the fluorescent emission of each sensor. In each case, both analyte sensitive ("sensor"), and analyte insensitive ("reference") fluorescent properties of the dyes were measured to minimize unwanted drift and interference. Dichroic splitters were used to couple individual fiber/dye assemblies to a pair of photodiodes/filter sets ($O_2$ sensor) or a pair of LED/filter sets (pH and $CO_2$).

TABLE 1

Analyte sensor excitation and emission wavelengths

| | Sensor Excitation | Reference Excitation | Sensor Emission | Reference Emission |
|---|---|---|---|---|
| Oxygen | 488 nm | 488 nm | 610 nm | 535 nm |
| PH | 464 nm | 435 nm | 530 nm | 530 nm |
| $CO_2$ | 460 nm | 415 nm | 530 nm | 530 nm |

Each sensor was calibrated once using multiple measurement points and a polynomial regression method to establish a nonlinear calibration curve.

Sensors were then recalibrated daily using a two-point calibration method. pH sensors were calibrated by sampling the optical response while submerged in a buffer solution with pH of 6.0 for 2 minutes, then in a solution with pH 8, each for two minutes. Oxygen and $CO_2$ sensors were calibrated using data points acquired while both sensors were submerged for two minutes in a saline bath purged with room air, followed by a bath purged with 10% $CO_2$/90% $N_2$.

During a typical assay, approximately $1.5 \times 10^5$ cells were placed in the vessel along with 500 μl of liquid media, resulting in a cell density of $3 \times 10^5$ cells/ml. To perform a measurement, the cylindrical cover was temporarily inserted into the vessel. The cover displaced liquid media, but not cells, to form a smaller sample chamber with a volume of 160 μl and a therefore a cell density of approximately $1 \times 10^6$ cells/ml. This resulted in more than a 6× increase in the rate of change of analytes within the media in proximity to the biosensors.

In order to evaluate the ability of the prototype device to reproducibly measure extracellular analytes flux rates, $1.5 \times 10^5$ undifferentiated C2C12 murine skeletal muscle cells (obtained from ATCC, Manassas, Va.) were seeded on each of eight separate 12 mm diameter polycarbonate membranes which were then incubated at 37° C. for a period of 12 hours.

In a sequence of tests, wells were removed from the incubator, inspected visually, and placed into the measurement device. 160 μl of bicarbonate ($NaHCO_3$)-free DMEM Medium (obtained from Specialty Media, Phillipsburg, N.J.) was then added, and the device was assembled to form an enclosed sample chamber. The concentration of each analyte (partial pressures of $O_2$ and $CO_2$, and pH as an indicator of proton concentration) was then measured every 8 seconds for a period of 20 minutes, and the average rate of change of each analyte was calculated over a four minute period from t=12 minutes to t=16 minutes.

To determine the extracellular flux rates of $O_2$ and $CO_2$, the rates of change of partial pressures were divided by volume of each analytes available in the media (moles) to result in a value expressed in nmol/minute. The rate of acidification was expressed in mpH units/min (multiplied by 20 for scaling on the chart), but can easily be shown as protons per minute by calculating the number of available electrons in the media buffer within the known sample volume.

Figure 6:
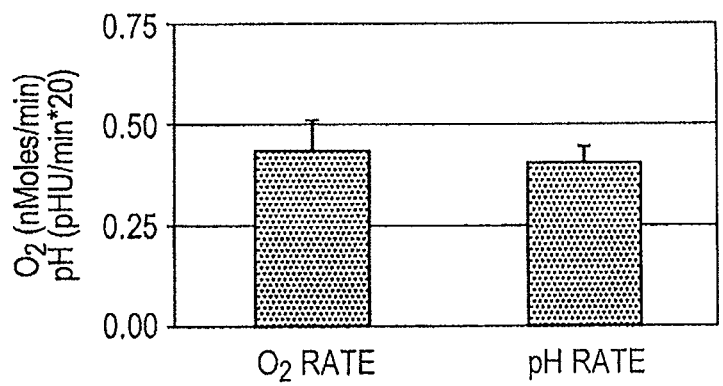
FIG. 6 is a graph showing the result of a study of the oxygen consumption and extracellular acidification rates of typical mammalian cells, depicting the mean and standard deviation of a series of eight separate measurements using one embodiment of the invention.

The mean and standard deviation of the dissolved oxygen and pH decay rates for the series of eight tests are shown in FIG. 6. As shown, these flux rates are highly reproducible in the prototype device.

Example 2

Measurement of Basal Respiration and Acidification Rates for Various Cell Densities The experimental device described in Example 1 was used to investigate the relationship between cell number and oxygen and $CO_2$ flux rates. Varying numbers ($1.0 \times 10^5$-$4.0 \times 10^5$) of C2C12 myoblasts were seeded on 12 mm diameter polycarbonate membranes (Corning Snapwell™) which were then incubated at 37° C. for a period of 12 hours.

Figure 7:
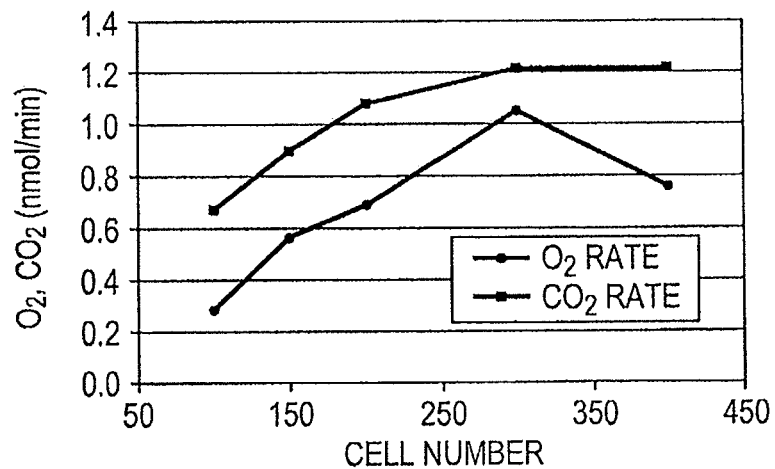
FIG. 7 is a graph showing the result of a study of the oxygen consumption and carbon dioxide evolution rates of various numbers of typical mammalian cells using one embodiment of the invention.

Wells were then removed from the incubator, inspected visually, and placed into the measurement device. 150 μl of $NaHCO_3$-free DMEM Medium (obtained from Specialty Media, Phillipsburg, N.J.) was then added, and the device was assembled to form an enclosed sample chamber. The concentration of each analyte was then measured every 5 seconds for a period of 20 minutes, and the average rate of change from t=10 minutes to t=20 minutes from start was computed. The resulting flux rates are shown in Table 2 and in graphical form in FIG. 7.

TABLE 2

Measuring Metabolic Analytes from Varying Titrations of C2C12 Myoblasts

| Cell # (000) | $O_2$ Rate | $CO_2$ Rate | pH Rate | $CO_2/O_2$ | $O_2$/pH |
|---|---|---|---|---|---|
| 400 | 0.77 | 1.22 | 0.023 | 0.88 | 0.33 |
| 300 | 1.06 | 1.22 | 0.021 | 1.15 | 0.50 |
| 200 | 0.70 | 1.08 | 0.019 | 0.93 | 0.35 |
| 150 | 0.57 | 0.90 | 0.021 | 1.63 | 0.26 |
| 100 | 0.29 | 0.68 | 0.013 | 2.36 | 0.22 |

The data in Table 2 shows, as expected, that increasing cell density increases analyte flux rates in a near-linear fashion for most cell densities. Above a density of $3 \times 10^5$ cells, oxygen flux did not increase as rapidly, presumably due to contact inhibition and crowding effects.

The device can therefore be used to evaluate the effect of high cell densities on metabolic rates.

Example 3

The Effect of 2,4 DNP on C2C12 Myoblasts

The chemical compound 2,4 DNP can be used to uncouple mitochondrial respiration from ATP synthesis by disassociating the linkage between the respiratory chain and the phosphorylation system. In the presence of this compound, it is known that oxygen consumption will increase dramatically, while proton flux remains relatively constant.

In this experiment, C2C12 myoblasts were seeded on 12 mm diameter polycarbonate membranes and incubated for 12 hours. Wells were then removed from the incubator, inspected visually, and placed into the measurement device. 160 µl of $NaHCO_3$-free DMEM medium was then added, and the device was assembled to form an enclosed sample chamber.

Figure 8:
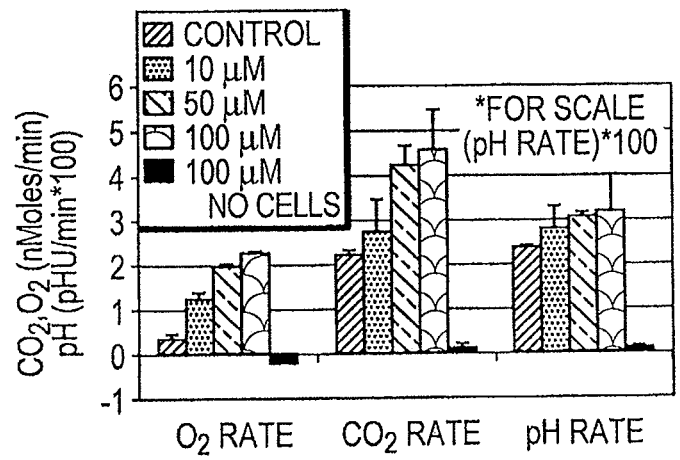
FIG. 8 is a graph showing the result of a study of the effect of the chemical compound 2,4, DNP on the rates of oxygen consumption, carbon dioxide evolution, Wand extracellular acidification of typical mammalian cells using one embodiment of the invention.

The dissolved concentrations of $O_2$ and $CO_2$, and the pH in the media were then measured every 5 seconds for a period of 20 minutes in order to determine a control baseline for each analyte flux. Once the baseline was established, a sequence of experiments were performed where varying doses of 2,4 DNP (obtained from Sigma, St. Louis Mo.) were added to the cell media and a 20 minute measurement of analyte flux rates was performed. A control experiment was also performed using the highest dose of 2,4 DNP, but without cells. The data from the dose response is shown in Table 3 and FIG. 8.

TABLE 3

Effect of 2,4DNP on C2C12 Myoblasts

| 2,4 DNP Dose (µM) | $O_2$ Rate (nM/min) | $CO_2$ Rate (nM/min) | pH Rate (pH/min) | $CO_2/O_2$ | $O_2$/pH |
|---|---|---|---|---|---|
| 0 | 0.38 | 2.22 | 0.024 | 5.83 | 0.16 |
| 10 | 1.26 | 2.78 | 0.028 | 2.18 | 0.46 |
| 50 | 1.99 | 4.24 | 0.031 | 2.13 | 0.64 |
| 100 | 2.30 | 4.59 | 0.032 | 2.00 | 0.73 |
| 100 No Cells | −0.18 | 0.15 | 0.001 | −0.84 | −1.30 |

The data in Table 3 shows that as predicted, treatment with 2,4 DNP causes a dose-dependent increase in $O_2$ consumption rates while having little effect on extracellular acidification.

Example 4

The Effect of Rotenone on C2C12 Myoblasts

Rotenone is known to inhibit cellular respiration by blocking NADH dehydrogenase in the respiratory chain. C2C12 Myoblasts were used to show this effect. $1.5 \times 10^5$ C2C12 myoblasts were seeded on membranes, incubated and placed in the measurement system along with 150 µl $NaHCO_3$-free DMEM medium of as described in Example 3.

Figure 9:
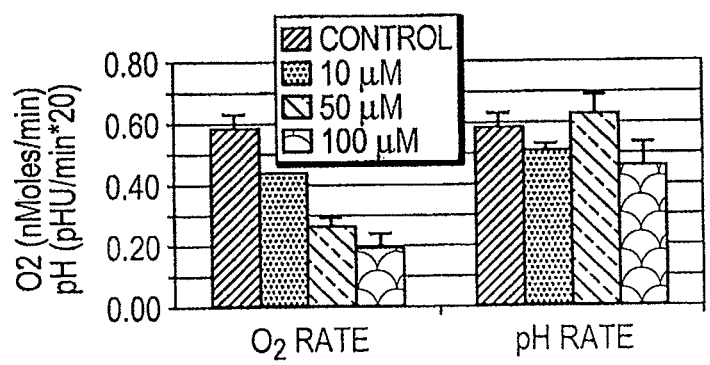
FIG. 9 is a graph showing the result of a study of the effect of the chemical compound Rotenone on the rates of oxygen consumption and extracellular acidification of typical mammalian cells using one embodiment of the invention.

The dissolved concentrations of $O_2$ and $CO_2$, and the pH in the media were then measured every 5 seconds for a period of 20 minutes in order to determine a control baseline for each analyte flux. Once the baseline was established, a sequence of experiments were performed where varying doses of Rotenone (obtained from Sigma, St. Louis Mo.) were added to the cell media and a 20 minute measurement of analyte flux rates was performed. A control experiment was also performed using the highest dose of Rotenone, but without cells. The data from the dose response is shown in Table 4 and FIG. 9.

TABLE 4

Effect of Rotenone on C2C12 Myoblasts

| Rotenone Dose | $O_2$ Rate | $CO_2$ Rate | pH Rate | $CO_2/O_2$ | $O_2$/pH |
|---|---|---|---|---|---|
| 0 | 0.58 | 1.50 | 0.027 | 2.56 | 0.22 |
| 25 | 0.44 | 1.76 | 0.026 | 4.00 | 0.17 |
| 50 | 0.26 | 2.08 | 0.031 | 8.02 | 0.08 |
| 100 | 0.19 | 2.34 | 0.023 | 12.18 | 0.09 |
| 200 | 0.04 | 2.24 | 0.027 | 69.84 | 0.02 |
| 200-No Cells | −0.07 | 0.14 | 0.001 | 7.51 | −0.51 |

The data in Table 4 demonstrates that, as expected, treatment with Rotenone causes a dose-dependent decrease in $O_2$ consumption rate in these cells.

Example 5

Measurement of Respiration and Acidification Rate Changes Resulting from Cell Proliferation The experimental device described in Example 1 was used to investigate the relationship between cell proliferation and oxygen, $CO_2$ and proton flux rates. $5.0 \times 10^4$ C2C12 myoblasts were seeded on 12 mm diameter polycarbonate membranes and then incubated at 37° C. 12 hours after being seeded, cells were placed in DMEM serum-free media (Gibco, Carlsbad, Calif.) to inhibit proliferation. After 24 hours, half of the cells were switched to DMEM serum-containing media to stimulate proliferation, while the other half were maintained in serum-free media.

Figure 10:
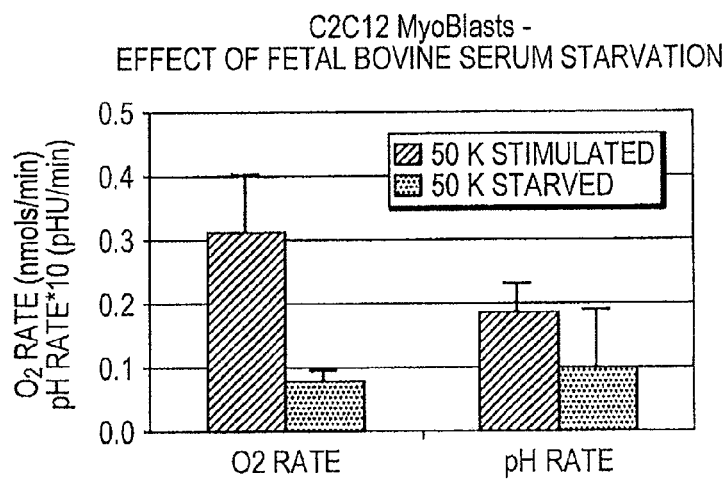
FIG. 10 is a graph showing the result of a study of the effect of cell proliferation on oxygen consumption and extracellular acidification using one embodiment of the invention.

Wells were then removed from the incubator, inspected visually, and placed into the measurement device. 57 µl of $NaHCO_3$-free DMEM Medium (obtained from Specialty Media, Phillipsburg, N.J.) was then added and the device was assembled to form an enclosed sample chamber. The concentration of each analytes was then measured every 8 seconds for a period of 20 minutes, and the average rate of decay from t=10 minutes to t=20 minutes from start was computed. The resulting flux rates are shown in Table 5 and in graphical form in FIG. 10.

TABLE 5

Effect of cell proliferation on extracellular analyte fluxes

|  | O2 Rate (nMoles/min) | PH Rate*10 (PHU/min) |
|---|---|---|
| 50 K Stimulated | 0.311 +/− 0.091 | 0.188 +/− 0.020 |
| 50 K Starved | 0.082 +/− 0.019 | 0.102 +/− 0.050 |

The data in Table 5 demonstrates that, as expected, cell proliferation results in an increase in oxygen consumption and the rate of extracellular acidification.

Example 6

Measurement of G-Protein Coupled Receptor Activation in CHO-M3 Cells

Previous studies have shown that stimulation of transmembrane receptors often causes a rapid increase in extracellular acidification rate, resulting primarily from acute activation of ion exchange pumps. In this experiment, the prototype device was used to detect a change in extracellular acidification rate following treatment of cells with a receptor agonist.

Chinese hamster ovary (CHO) cells were transfected to over-express the muscarinic receptor subtype m3. The prototype device described in Example 1 was then used to monitor $O_2$ consumption, $CO_2$ production, and extracellular acidification rates, following treatment with the well-known, general acetylcholine receptor agonist, Carbachol.

Materials and Methods: Cell culture reagents were obtained from Gibco BRL (Grand Island, N.Y.). Carbachol was purchased from Sigma Chemical Co. (St. Louis, Mo.). Bicarbonate-free DMEM medium was obtained from Specialty. Media (Phillipsburg, N.J.). Polycarbonate membrane snapwells (12 mm diameter, 3 μm pore size) were obtained from Corning (Corning, N.Y.). CHO cells expressing m3-muscarinic receptors (CHO-M3 cells) were obtained from the American Type Tissue Culture (ATCC; Manassas, Va.). Cells were cultured in Ham's F-12 medium supplemented with 10% fetal bovine serum (Hyclone), 1% GlutaMax and 0.1% Gentamicin and were maintained in a 5% $CO_2$ incubator. Cells were subcultured when they reached 80% confluency. CHO-M3 cells were seeded at a density of $2\times10^5$ onto a snapwell 24 hours prior to use. Immediately prior to testing, cells on snapwells were switched to bicarbonate-free DMEM medium combined with 3.7 g/l NaCl to maintain osmolarity (medium pH 7.4-7.5).

Protocol Description: Probes were calibrated immediately prior to testing. The bottom of the test vessel was filled with bicarbonate-free medium. The snapwell was removed from a 5% CO2 incubator, and the regular growth medium (Ham's F-12) was replaced with bicarbonate-free DMEM medium. Thereafter, the snapwell was placed into the test vessel. Bicarbonate-free medium was pipetted onto the top of the snapwell, and the cover piece of the test vessel was placed gently on top of the snapwell and screwed into place, compressing the assembly. The probe software was started, and the pH, $CO_2$ and $O_2$ analytes were measured over the next 3.5 hours. Following the initial 1.5 hours of perfusion at a rate of 78 μl/min, a series of stop flow (10 minutes each) and medium re-perfusion (10 minutes each, 78 μl/min) cycles were started. During the last 2 minutes of medium re-perfusion cycle number 5, 100 μM carbachol was perfused across the snapwell. During re-perfusion number 6, bicarbonate-free MEM medium was once again perfused across the snapwell. A rate of change for the analytes was calculated during each stop flow cycle.

Results:
CHO-M3 Baseline Followed by 100 μM Carbachol Treatment

Figure 11:
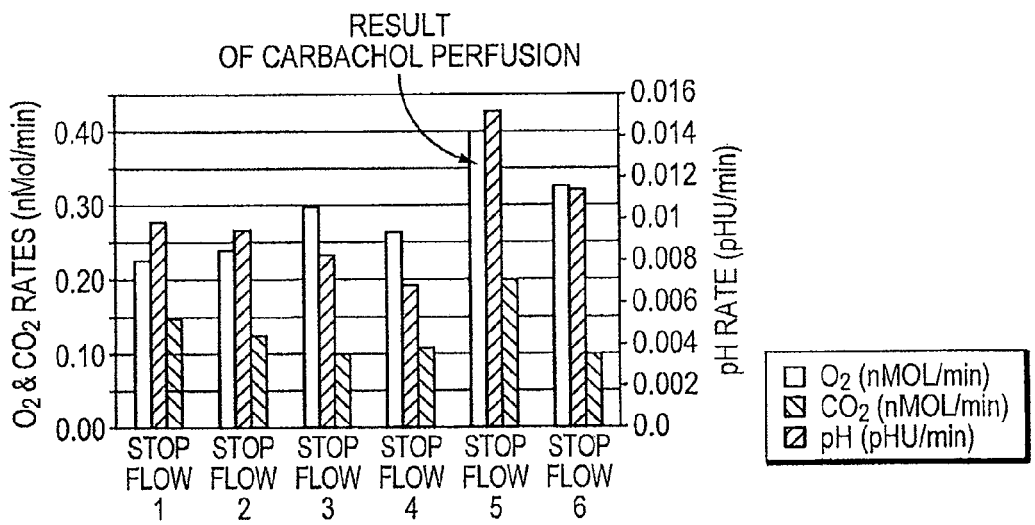
FIG. 11 is a graph showing the result of a study of the effect of the chemical compound Carbachol on the rate of extracellular acidification of typical mammalian cells using one embodiment of the invention.

The first four series of perfusion/stop flow cycles were done to establish a noise band on the three analytes prior to carbachol treatment during perfusion number 5. Bicarbonate-free medium re-perfusion during per perfusion number 6 and the rates calculated during stop flow number 6 were to assess potential continuing post-carbachol treatment effects on analytes' rates. Resulting data are shown below in Table 6 and in FIG. 11.

TABLE 6

Effect of carbachol exposure on oxygen consumption, carbon dioxide evolution, and extracellular evolution

| Rate Summary | $O_2$ (nMol/min) | $CO_2$ (nMol/min) | pH (PHU/min) | $O_2/CO_2$ Ratio | $O2/pH$ Ratio |
|---|---|---|---|---|---|
| Stop Flow 1 | 0.23 | 0.15 | 0.01 | 1.53 | 0.23 |
| Stop Flow 2 | 0.24 | 0.12 | 0.01 | 1.93 | 0.25 |
| Stop Flow 3 | 0.30 | 0.10 | 0.01 | 3.04 | 0.36 |
| Stop Flow 4 | 0.27 | 0.11 | 0.01 | 2.45 | 0.38 |
| Stop Flow 5 | 0.40 | 0.20 | 0.02 | 1.99 | 0.26 |
| Stop Flow 6 | 0.33 | 0.10 | 0.01 | 3.34 | 0.29 |

Average baseline values compared to treatment values illustrate that a 2-minute exposure of CHO-M3 cells to carbachol resulted in a doubling in the pH rate (0.01 PHU/min vs 0.02 PHU/min), though $O_2$ and $CO_2$ rates also demonstrated increases above baseline levels (see below). Post-treatment rates generated during stop flow period number 6 essentially returned to pre-treatment values.

Example 7

Comparison of Measured Analyte Fluxes with and without the Temporary Formation of a Sample Chamber The temporary formation of a sample chamber within a larger vessel, and containing an effectively high concentration of cells, is a characteristic for the instant invention.

In order to demonstrate this principle, a cylindrical vessel of approximately 12 mm in diameter and 10 mm in height was constructed from polycarbonate material. Fluorescent sensors capable of measuring partial pressures of $O_2$ and $CO_2$, and a sensor capable of measuring pH, were installed in the bottom of the vessel and calibrated as described previously. A cylindrical cover was also fabricated from polycarbonate material, with a diameter to accommodate insertion into the vessel, in order to provide a gas-impermeable cover and to reduce the enclosed volume of the vessel as required. A cylindrical spacer of 0.5 mm in height was also fabricated, with a diameter to accommodate insertion in the bottom of the vessel, thus providing a stop for the cover at a precise location.

Approximately $1\times10^5$ C2C12 myoblast cells was prepared as described previously. The cells were placed within the vessel along with approximately 1 ml of cell growth media. The partial pressure of oxygen within the cell media was measured continuously using a calibrated fluorescent probe. The rate of change of $pO_2$ was then calculated from the difference between the $pO_2$ values at 12 and 16 minutes from the start of the experiment.

A cylindrical cover was then placed on the surface of the cell media in order to inhibit the influx of oxygen from the ambient air. This also reduced the volume of media exposed to the cells to approximately 130 μl. Again, the $pO_2$ values at 12 and 16 minutes from the start of the experiment were measured and recorded.

The cylindrical cover was then lowered within the vessel (to rest on the spacer) so as to reduce the volume of media exposed to the cells to approximately 57 μl. Again, the $pO_2$ values at 12 and 16 minutes from the start of the experiment were measured and recorded.

Figure 12:
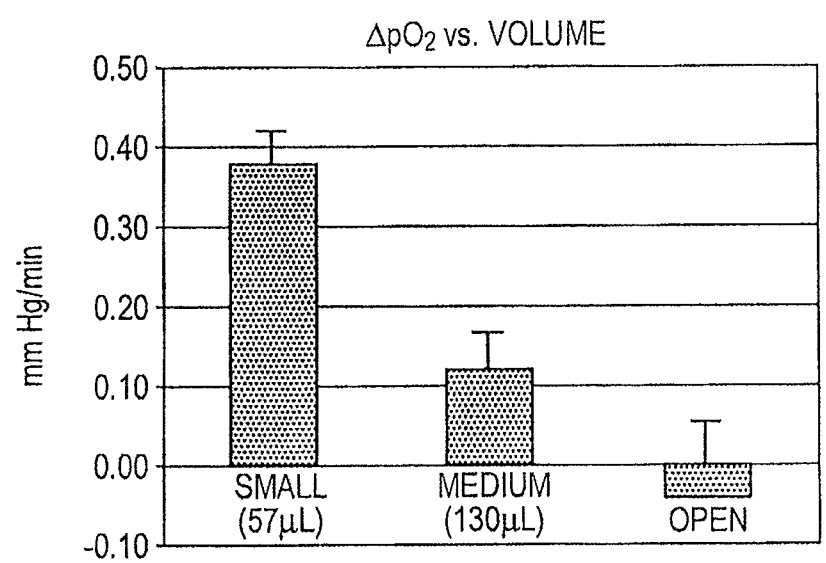
FIG. 12 is a graph showing a comparison of the measured rates of oxygen consumption of typical mammalian cells in a vessel with, and without, the formation of a small, enclosed sample chamber using one embodiment of the invention.

The measured rates of change of $pO_2$ within the cell media for the three conditions are shown in tabular form in Table 7 and in graphical form in FIG. 12.

TABLE 7

Oxygen depletion rates in a four minute interval, with and without the formation of an enclosed sample chamber (n = 3)

| Volume | ΔpO2 | s.d. | % CV |
|---|---|---|---|
| Small (57 μL) | 0.38 | 0.04 | 10% |
| Medium (130 μL) | 0.12 | 0.05 | 38% |
| Open | −0.04 | 0.10 | n/a |

This experiment demonstrates that the formation of an enclosed sample chamber, sealed from ambient air and containing a high density of cells, generates flux rates sufficient to provide a rapid measurement with a high signal-to-noise ratio.

It is apparent that many modifications and variations of this invention as hereinabove set forth may be made without departing from the spirit and scope of the present invention and the above examples are not intended to in any way to limit the present invention but are merely exemplary. The foregoing embodiments are therefore to be considered in all respects illustrative rather than limiting on the invention described herein.

What is claimed is:

1. An apparatus for analyzing cells disposed in media in multiple wells of a multi-well plate by analysis of solutes in the medium absorbed by or secreted from the cells, the apparatus comprising:

an array of fluorescent sensors spaced apart so as to match a spacing of at least a portion of the multiple wells;

motorized actuators on which the fluorescent sensors are mounted, to control insertion of the fluorescent sensors into and retraction from respective wells of the multi-well plate, wherein the sensors acquire, when in sensing communication with the media in the wells, optical signals indicative of concentrations of a solute in the medium disposed in the wells from which an attribute of the cells may be measured, the actuators being moveable in a vertical direction to move the fluorescent sensors relative to the wells to and from a sensing position close to the cells;

an electro-optical measurement system in communication with the sensors to interrogate the sensors when in sensing communication with the media in the wells;

a readout to transmit the signals from the sensors to the electro-optical measurement system; and a stage to hold the multi-well plate below the motorized actuators and allow relative movement of the motorized actuators and the multi-well plate with respect to each other.

2. The apparatus of claim 1 wherein the readout comprises optical fibers.

3. The apparatus of claim 1 wherein the electro-optical measurement system comprises an illumination source and an optical detector.

4. The apparatus of claim 1 wherein the electro-optical measurement system comprises at least one of a spectral filter or a signal-processing component.

5. The apparatus of claim 1 wherein the electro-optical measurement system comprises an external electronic measurement system coupled to the optical and measurement components.

6. The apparatus of claim 1 further comprising a computer in electrical communication with the electro-optical measurement system.

7. The apparatus of claim 6 wherein the computer is configured to perform at least one of an actuation function, a calibration function, or a measurement function.

8. The apparatus of claim 1, wherein the actuators are further moveable in a horizontal direction to enable movement of the fluorescent sensors relative to the wells to and from a sensing position close to the cells.

* * * * *